(12) United States Patent
Martin et al.

(10) Patent No.: US 7,251,022 B2
(45) Date of Patent: Jul. 31, 2007

(54) DUAL FIBER MICROPROBE FOR MAPPING ELEMENTAL DISTRIBUTIONS IN BIOLOGICAL CELLS

(75) Inventors: Rodger C. Martin, Powell, TN (US); Madhavi Z. Martin, Powell, TN (US)

(73) Assignee: UT-Battelle, LLC, Oak Ridge, TN (US)

(*) Notice: Subject to any disclaimer, the term of this patent is extended or adjusted under 35 U.S.C. 154(b) by 105 days.

(21) Appl. No.: 11/240,264

(22) Filed: Sep. 30, 2005

(65) Prior Publication Data
US 2007/0076200 A1    Apr. 5, 2007

(51) Int. Cl.
G01J 3/30 (2006.01)
G01N 21/63 (2006.01)

(52) U.S. Cl. .................. 356/72; 356/318
(58) Field of Classification Search ........ 356/317, 356/318
See application file for complete search history.

(56) References Cited

U.S. PATENT DOCUMENTS

2004/0183018 A1  9/2004  Zhou et al.
2005/0200843 A1  9/2005  Kumar et al.

FOREIGN PATENT DOCUMENTS

JP   2005-140529   * 6/2005

* cited by examiner

Primary Examiner—F. L. Evans
(74) Attorney, Agent, or Firm—Joseph A. Marosco; James M. Spicer

(57) ABSTRACT

Laser-induced breakdown spectroscopy (LIBS) is applied on a microscale for in situ elemental analysis and spatial mapping in biological cells. A high power laser beam is focused onto a cell surface using a dual branching optical fiber probe for optical excitation of the cell constituents. Dual spectrometers and ICCD detectors capture the emission spectra from the excited cell(s). Repeated probing or repositioning of the laser beam with respect to the cell can provide 2-D or 3-D mapping of the cell.

25 Claims, 5 Drawing Sheets

DUAL FIBER MICROPROBE FOR MAPPING ELEMENTAL DISTRIBUTIONS IN BIOLOGICAL CELLS

RESEARCH OR DEVELOPMENT

The United States Government has rights in this invention pursuant to Contract No. DE-AC05-00OR22725 between the United States Department of Energy and UT-Battelle, LLC.

BACKGROUND OF THE INVENTION

1. Field of the Invention

The invention relates to laser-induced breakdown spectroscopy (LIBS), and more particularly to an apparatus suitable for conducting microscale LIBS analyses of biological cells, the cell interiors, and the cell environs.

2. Description of the Prior Art

The analytical technique of laser-induced breakdown spectroscopy (LIBS), also called laser-induced plasma spectroscopy (LIPS) or laser plasma spectroscopy (LPS), focuses a high-power laser beam onto a sample surface, with each pulse sparking on and vaporizing a small mass (sub-microgram) of sample and creating a microplasma. As the constituents of the plasma plume de-excite during cooling, they give off light with wavelengths characteristic of the elemental constituents of the plasma. By analyzing this light, the sample contents can be determined and often quantified, without the need for sample preparation or long analytical lead times.

Detection of most of the elements of the periodic table using LIBS has been demonstrated for a variety of samples and sample matrices (solid, liquid, aerosol, and gas phase). For example, LIBS was established at ORNL by the co-inventors and others during the development of in-situ, real-time air monitors for hazardous metals in atmospheric emissions.

Current analyses of pharmaceutical distributions within cells are very tedious. Conventional analyses of average elemental distributions within cells, such as boron distributions between cytoplasm and nucleus, typically involve digestion of the cells, followed by fractionation and separate analyses of nuclear and cytoplasmic components. More expensive analytical techniques such as inductively-coupled plasma mass spectrometry (ICP-MS) have greater sensitivity (~ppb) than required for meaningful boron distributions for NCT applications (~tens of ppm). Analytical results are complicated by the potential for cross-contamination between the fractionated cellular components.

Others have attempted to use synchrotron x-ray spectroscopy, secondary ion mass spectrometry (SIMS), and more complex laser-based techniques on dried cells, but all are either very tedious, require demanding and lengthy data analysis, or are of questionable analytical accuracy. None of these techniques can provide the rapid, accurate analyses suitable for statistically meaningful sampling of a large number of cells that is made possible by the present LIBS invention.

Conventional LIBS has been developed for the characterization of biological samples on a macroscopic scale; i.e., a large laser spot size ($\geq 30$ μm) with random placement of the beam vaporizing multicellular material. Macroscopic biological applications of LIBS have included trace mineral analyses of skin tissue, fingernails, and teeth, as well as plants and other samples. There have been no reports of LIBS analyses on the subcellular level, and none for the uptake and distribution of pharmaceutical agents. The present invention extends LIBS apparatus capability to single cells on the cellular and subcellular level.

BRIEF SUMMARY OF THE INVENTION

In a preferred embodiment, the invention is a laser-induced breakdown spectroscopy (LIBS) apparatus for a sample comprising: a pulsed laser light source; an optical fiber probe, the optical fiber probe bifurcated into two branch probes, each branch probe capable of passing excitation light from the laser and collected light from the sample or its environs; and first and second spectrometer/ICCD systems; the first and second spectrometer/ICCD systems capable of producing emission spectrums of the collected light from the two branch probes.

DETAILED DESCRIPTION OF THE INVENTION

Figure 1:
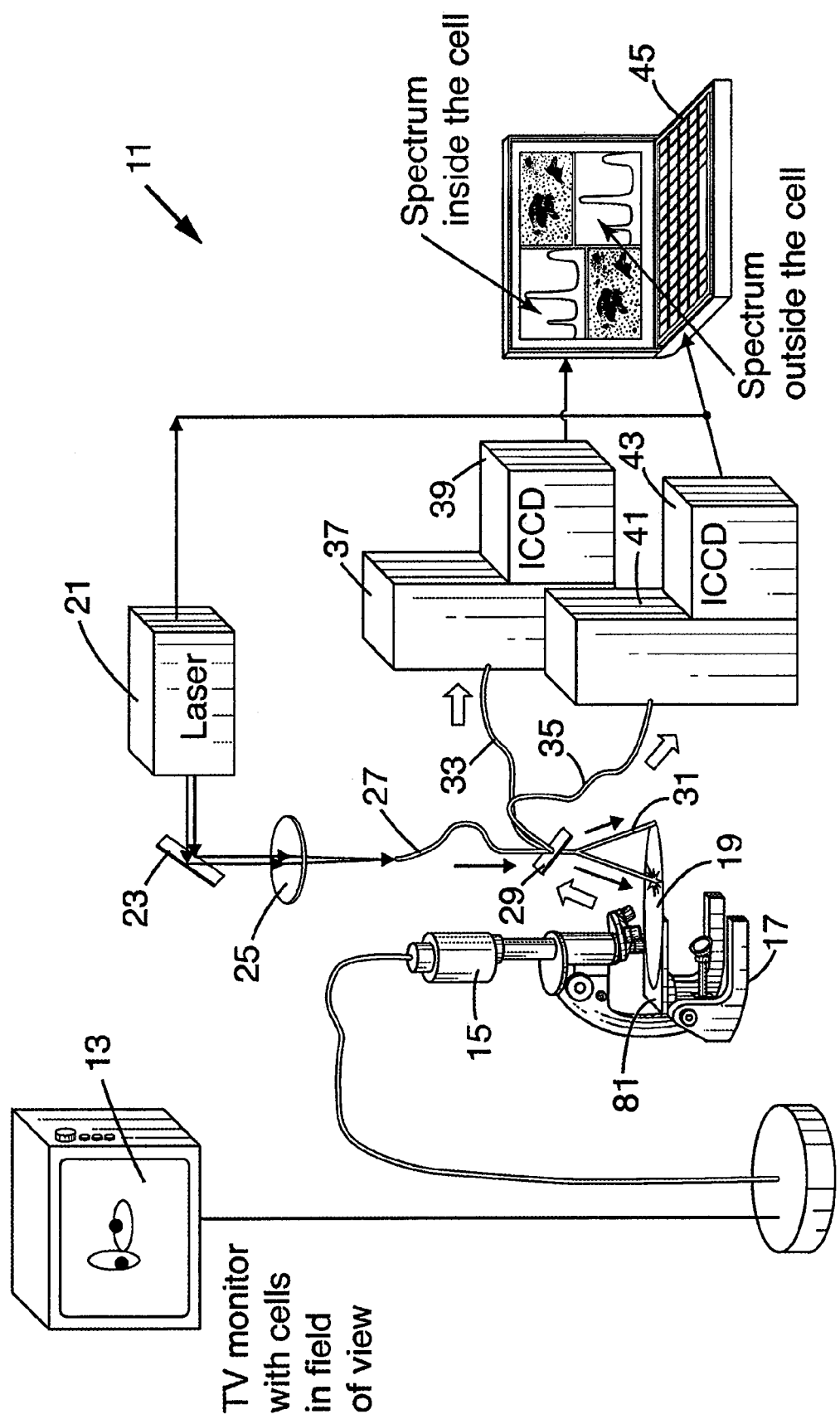
FIG. 1 is an illustration of a first embodiment of the dual fiber microprobe apparatus of the present invention.

In a preferred embodiment, the dual fiber microprobe system 11 incorporates some standard LIBS components: a laser 21, wavelength specific laser mirror 23, not one but two spectrometers 37, 41, two intensified charge coupled devices (ICCD) detector devices 39, 43, dichroic filter 29, and associated optics (with or without fiber optic transmission of the laser beam, as by the fiber optic cable 27 shown in FIG. 1). The collected light from a bifurcated (dual branching) optical fiber probe 31 is transmitted to the spectrometers 37, 41 via fiber optic cables 33, 35. Laser spot reducing optics (biconvex focusing lens 25) have been incorporated. This element is able to reduce the laser spot size down to ~10 μm.

A microscope 17, digital camera 15, and TV monitor 13 may be employed for viewing the sample 19 and the laser spot placement. The laser 21 is a pulsed laser, usually a Nd:YAG laser that has laser emission wavelengths at 266, 532, and 1064 nm. The laser light is coupled into the optical fiber probe 31 that is bifurcated into dual fiber optical branch probes 51, 61.

In a typical application of the microprobe system 11, one of the branch probes (51) will excite and collect the light emitted via plasma emission from inside of a single cell, and the other branch probe (61) will excite and collect light emitted via plasma emission from the cell environs. The collected light from the two plasma excited sites is then simultaneously collected by the two spectrometers 37, 41 attached respectively to the two ICCD detectors 39, 43. A computer 45 may then be used to calculate and plot the emission spectrums (intensity of the emitted light vs. wave length) on a single-computer screen. When the system 11 is operated in this manner, the chemical mapping inside (intracellular) and chemical probing outside (extra-cellular) information can be simultaneously viewed.

Figure 2:
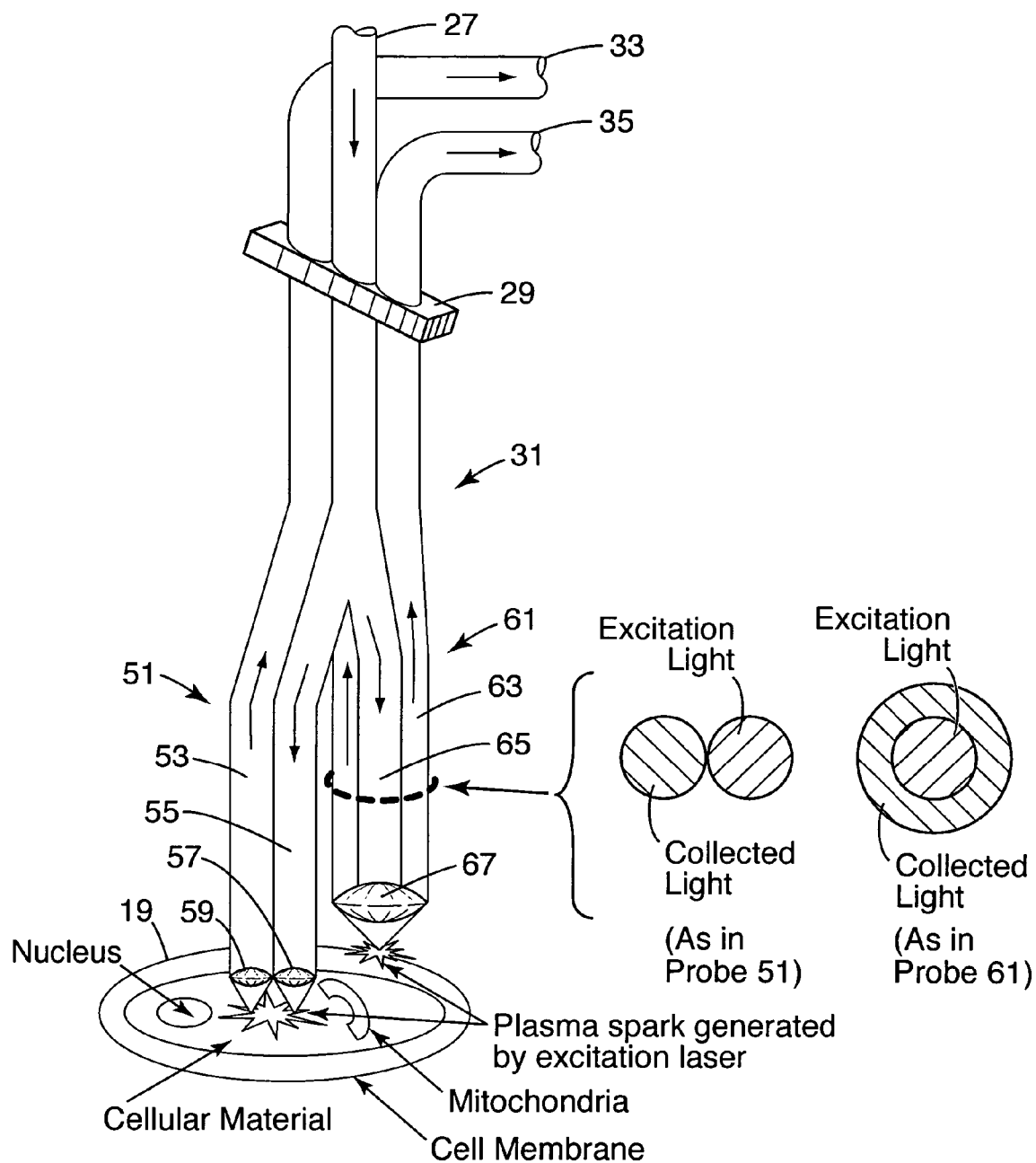
FIG. 2 is an illustration of a bifurcated (dual branching) optical fiber probe as used in the above embodiment.

FIG. 2 shows the bifurcated optical fiber probe 31 in detail. It is branched into two probes 51, 61 that produce simultaneous plasma excitations in the sample undergoing LIBS analysis from a single pulse of the laser 21. One branch probe may be used to plasma excite and map inside a biological cell sample (as shown by fiber 51, for example), and the other fiber (61) may be used to plasma excite elsewhere, in the cell, at the cell boundary, outside the cell, in another cell, etc. This allows monitoring the change in the cellular contents and specific elements that will be ejected from the interior to the immediate exterior. Certain diseases have shown to cause the excess buildup of certain elements out side the cell walls. Arthritis, for example, has calcium buildup outside the cells at specific sites.

A 3-D translation stage 81 mounted on the microscope 17 will allow plasma excitation to be carried out anywhere on or within the sample 19. One or both of the probes 51, 61 may be mounted on a movable element such as a rotational stage for additional movement and positioning on the probes. By such means, the probes are able to map the constituents inside the cell at different depths. For example, the emission spectrum for different x and y parameters will be collected and saved by the computer 45 at different depths of each cell.

If the probes 51, 61 are moved relative to the sample, it may be advantageous to time the various plasma excitations with respect to each other and with respect to cell location. For example, one probe may be timed to finish probing outside the wall of a cell for each depth z, and return to its original position when the other probe is ready to probe the next depth ($z_1$-$z_n$). This will result in a total 3-D spectra (elemental mapping) of a single cell and of its immediate vicinity.

This can be extended to mapping of two cells and their direct response to their environment surroundings, e.g., their extra-cellular regions. This will enable the researcher to chemically resolve other intracellular features, such as, nucleus, mitochondria, etc.

The apparatus as described above is capable of obtaining 3-D spectral information and reconstructing a 3-D chemical mapping of a single or multiple cells similar to 3-D imaging as done for a CAT scan.

FIG. 2 also shows that the probes 51, 61 can be configured in two different ways. A concentric probe configuration is shown by the probe 61. In probe 61, the excitation laser beam is delivered via a central light fiber 65, and the light from the emission spark is collected by the outer return light fiber 63 that surrounds the central fiber 65. In this configuration, a single plano-convex focusing lens 67, with a short focal length is sufficient to focus the excitation radiation and also for the collection of the light from the spark.

In probe 51, the excitation laser beam is delivered via a light fiber 55 that is adjacent the return light fiber 53. In this configuration, single plano-convex focusing lenses 57, 59, both with short focal lengths, are used to focus the excitation radiation and the collected radiation from the spark.

If it is desired to operate only one of the branch probes, the other branch probe may be capped to isolate the light that would otherwise propagate from it.

As a feasibility analysis of boron, LIBS was performed on a dried aqueous solution of 100 ppm by weight of gadolinium on a quartz substrate. Strong optical lines for gadolinium were observed. The limits of detection for gadolinium in this experimental configuration were not determined but are significantly lower than 100 ppm; i.e., significantly below the cellular concentrations required for effective neutron capture therapy based on gadolinium-containing pharmaceuticals.

Figure 4:
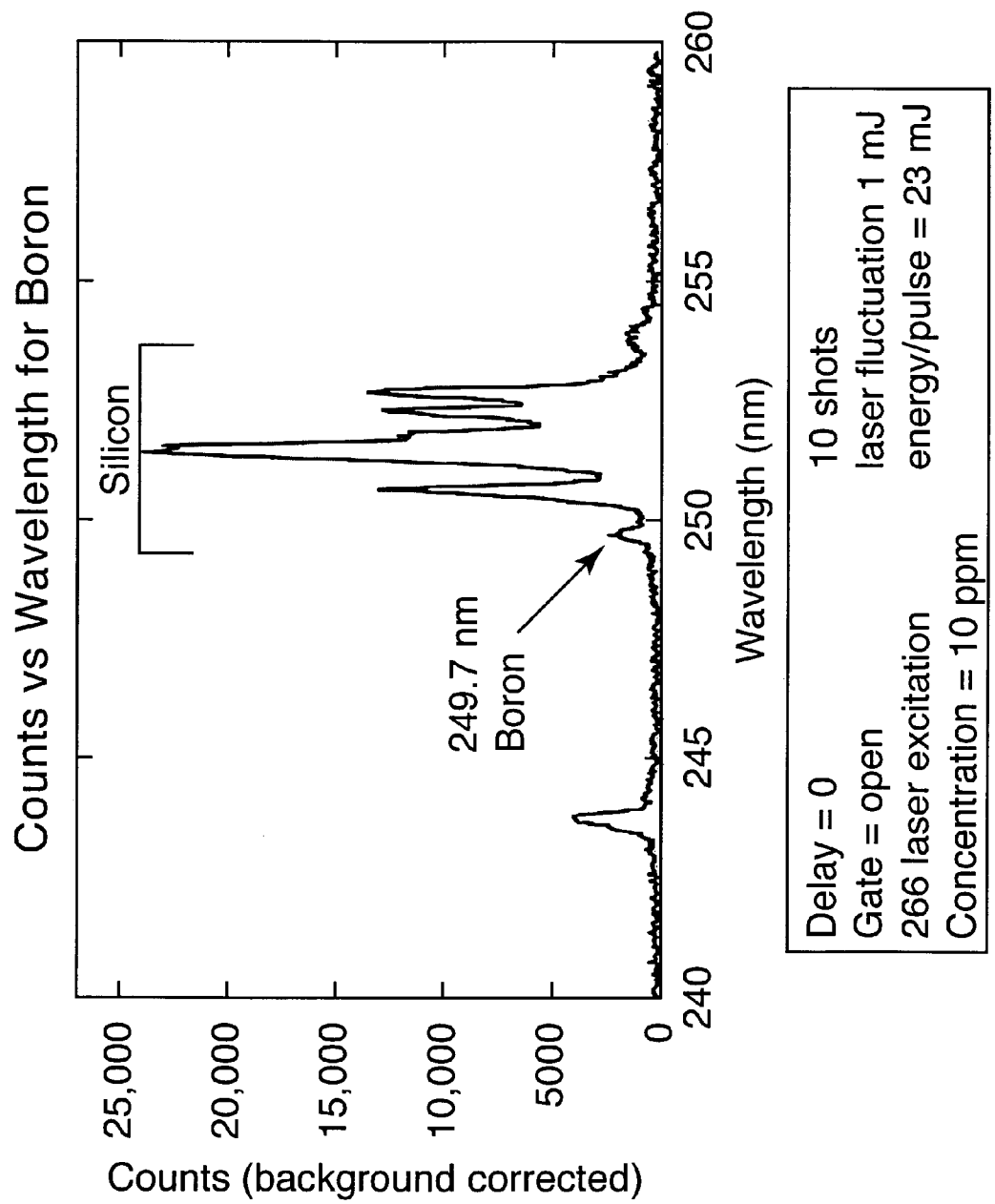
FIG. 4 is a LIBS analysis of a dried aqueous solution of boron to determine the limits of detection for boron in the experimental configuration.
Figure 5:
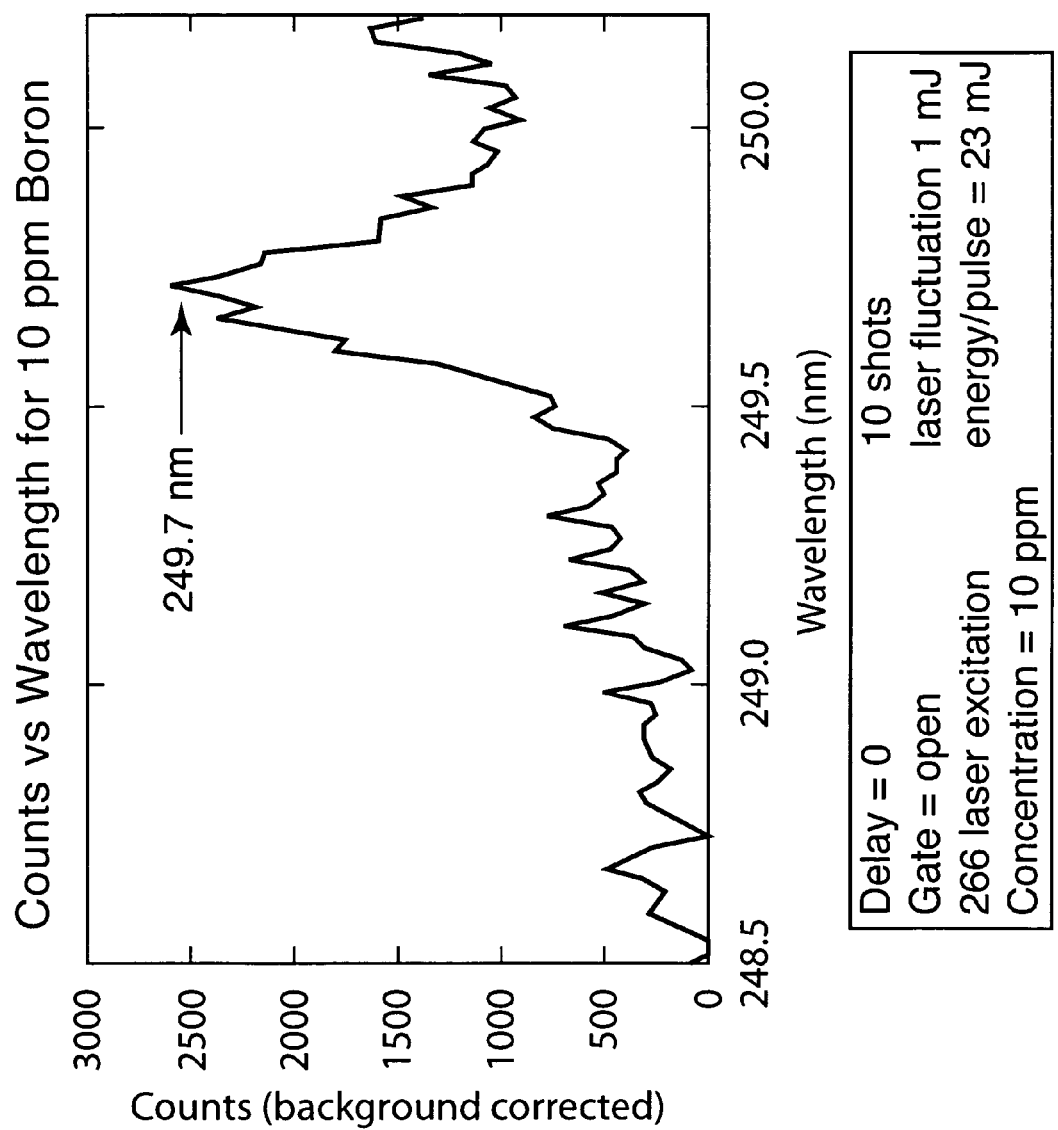
FIG. 5 is a LIBS analysis of a dried aqueous solution of gadolinium to determine the limits of detection for gadolinium in the experimental configuration.

LIBS was also performed on dried aqueous solutions of boron to determine the limits of detection for boron in the experimental configuration. The data in FIGS. 4 and 5 show that the dried solutions showed positive results for the presence of boron down to <2 ppm by weight, corresponding to detection of <10 ng of boron within the experimental configuration. (The concentration of 10 ppm stated in the figure captions corresponds to the total mass of the dissolved boron compound; the boron alone is <2 ppm.)

Because only a fraction of the total solution boron was analyzed due to sample and sampling geometries, the minimum limit of detection (LOD) of boron mass per laser shot has not been determined. Data were collected over 10 shots; one shot can detect boron at the nanogram range. Literature indicates that mass detection limits for LIBS are commonly in the picogram to subpicogram range, depending on element and sample matrix.

Literature values for boron uptake in cells range from 5 to >100 ppm of boron, and one study reports cellular boron loading ranging from 7 to 305 ng of boron per cell. The upper range of boron loadings are within our demonstrated LIBS detection capabilities, while 7 ng/cell is too low for intracellular mapping by LIBS. However, after determination of the LOD of LIBS for boron in these samples, lack of a positive boron signal will screen out those boron compounds whose cellular uptake is too low for practical use in NCT. Typically, boron concentrations of at least 30 ppm by weight in cells are required for meaningful neutron capture therapy (NCT) applications. Therefore, the collection of meaningful data does not require sub-ppm detection capabilities for boron.

For LIBS detection, some fraction of the total cellular mass will be vaporized for analysis per laser shot. The absolute mass limits of detection for each element of interest must be determined as a function of experimental configuration and laser spot size, and the spot size must then be optimized to detect the concentration range of interest for the element to be analyzed. Demonstration of the limits of elemental detection within the matrix as a function of laser spot size will permit determination of the smallest practical spot size for subcellular measurements and mapping of the elemental profiles within the cell.

The LIBS technique is the only one that operates at ambient atmospheric pressure, significantly simplifying hardware requirements compared to alternative techniques. Reducing the ambient pressure can improve sensitivity by removing atmospheric background effects. One paper has reported that a pressure of ~1 torr may provide optimum sensitivity for LIBS operation. This does not require high vacuum, thus simplifying the equipment and implementation.

Sample preparation is limited to, at most, drying the cells as needed, a simple and convenient technique. The accepted analytical method of cellular digestion followed by fractionation and analysis is very tedious in comparison.

Judicious application of microscopic imaging and sample positioning hardware will provide rapid in situ cell-by-cell and intracellular sampling, with near-real-time analytical results. No other techniques can promise this convenience. As a result, analysis times are greatly reduced over existing techniques.

After determination of the cell mass ablated per shot, this technique can be applied for shot-by-shot depth profiling into the cell matrix. One can then obtain 3-D profiles within and across the cell (bulk vs. surface concentrations, nuclear vs. cytoplasmic concentrations) as well as more accurate statistical analyses. No other demonstrated technique can provide unambiguous depth characterization without major effort.

In LIBS operation, it is possible to use a second, nearly overlapping laser pulse to enhance the efficiency of plasma ionization. This has been demonstrated to increase sensitivity by an order of magnitude for several elements. In the 1980's, the limit of detection (LOD) of boron in a water solution improved by over an order of magnitude using a dual pulse technique. This technique can be applied to lower the detectable limit of boron in cells.

A commercial instrument designed for laser ablation on the scale of one micrometer can be adapted for direct detection of optical emissions, i.e., set up for LIBS analysis, rather than incorporating ICP-MS or ICP-AES detection or using a LAMMA technique.

Figure 3:
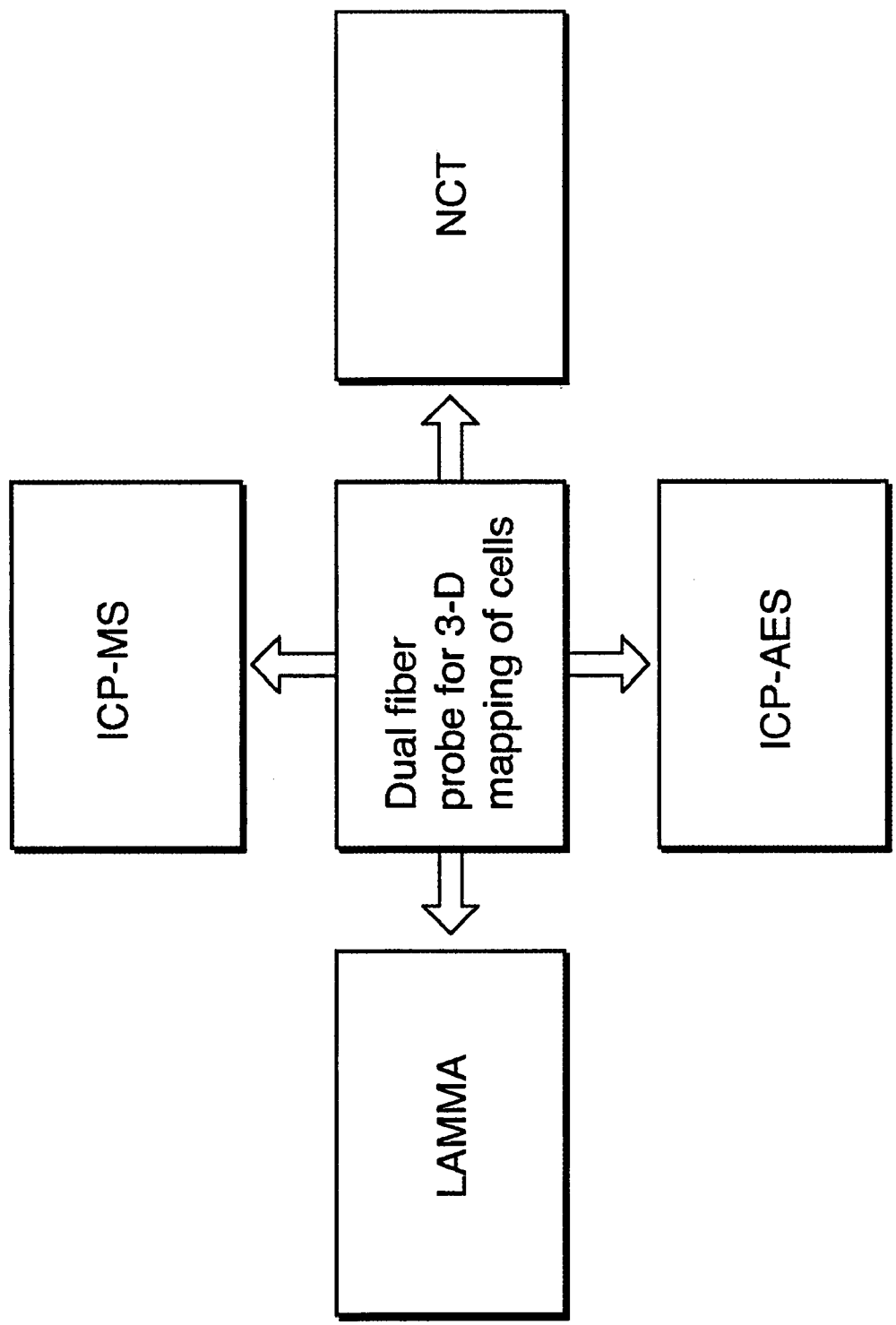
FIG. 3 is an illustration of the extension of the present invention into existing analytical methods.

LIBS can be used in conjunction with other microanalytical detection techniques. Some of these are inductively-coupled plasma mass spectrometry (ICP-MS) systems, neutron capture therapy (NCT) systems, inductively-coupled plasma atomic emission spectrometry (ICP-AES) systems, and laser microprobe mass analysis (LAMMA) systems, as illustrated in FIG. 3.

The aforementioned instrument can be used with ICP-MS, ICP-AES, or LAMMA to detect boron or gadolinium in cells, or to determine uptake and distribution of other pharmaceuticals, as this application has not been reported in the literature.

The detection of ablated cellular species can employ techniques other than direct optical emission when appropriate. For example, measurement of laser-induced fluorescence either directly from the laser plume, or using secondary excitation via a second, tunable laser, has been demonstrated for other samples and other elements. For boron, use of a diode laser for fluorescent excitation after ionization by ICP gave a reported LOD of 4 ppb. Laser vaporization followed by excitation by a tunable laser could reduce LODs for boron below those achievable by LIBS.

The elemental distribution of the human body indicates that over 50% of these elements can be analyzed using LIBS, if we assume a parts-per-million limit of detection.

A quick, in situ analytical capability would permit rapid screening of intracellular distribution for the multitude of experimental compounds developed for potential use in neutron capture therapy (NCT). Currently such a rapid screening capability does not exist.

More generally, this capability would permit rapid determination of inter- and intracellular distributions of pharmaceuticals, to determine their uptake and kinetics.

Beyond NCT applications, this capability can supplement the analysis of cell function as it relates to ionic and metallic transport and distribution between and within cells.

For diagnostics, this technique can provide a quick evaluation of cellular composition to determine elemental deficiencies and related dysfunction and/or disease screening. The literature reports a variety of trace minerals and elements whose deficiency or excess in humans can have significant biological effects, such as boron, calcium, chromium, copper, iron, silicon, and zinc, or potentially toxic elements such as aluminum, cadmium, lead, and mercury. LIBS has the capability for analysis of wet as well as dried samples.

The invention claimed is:

1. A laser-induced breakdown spectroscopy (LIBS) apparatus for a sample comprising:
    a pulsed laser light source;
    an optical fiber probe, said optical fiber probe bifurcated into two branch probes, each branch probe operable for passing excitation light from said laser and collected light from the sample or its environs; and
    first and second spectrometer/ICCD systems; said first and second spectrometer/ICCD systems operable for producing emission spectrums of the collected light from said two branch probes.

2. The apparatus of claim 1 wherein said optical fiber probe is bifurcated into more than two branch probes.

3. The apparatus of claim 1 further including a computer for displaying the emission spectrums produced by said first and second spectrometer/ICCD systems.

4. The apparatus of claim 1 further including a biconvex focusing lens in the light path between said laser and said two branch probes.

5. The apparatus of claim 1 further including a dichroic filter in the light path between said laser and said two branch probes.

6. The apparatus of claim 1 further including a microscope for holding the sample.

7. The apparatus of claim 6 wherein said microscope includes a 3-D translation stage for positioning the sample.

8. The apparatus of claim 6 further including a digital camera and TV monitor used in conjunction with said microscope.

9. The apparatus of claim 1 wherein said optical fiber probe further comprises an excitation light fiber and a collected light fiber, and wherein the excitation light fiber and the collected light fiber are adjacent one another.

10. The apparatus of claim 1 wherein said optical fiber probe further comprises an excitation light fiber and a collected light fiber, and wherein the excitation light fiber and the collected light fiber are concentric.

11. The apparatus of claim 1 wherein the emission spectrums are generated simultaneously.

12. The apparatus of claim 1 wherein at least one of said branch probes is positioned at the sample or its environs in a predetermined pattern.

13. The apparatus of claim 1 wherein at least one of said branch probes is arranged for ablating material from the sample for depth profiling.

14. The apparatus of claim 1 wherein the sample is an environmental sample.

15. The apparatus of claim 1 wherein the sample is a biological cell.

16. The apparatus of claim 1 wherein the sample is a biological cell containing boron.

17. The apparatus of claim 1 wherein the sample is a biological cell containing gadolinium.

18. The apparatus of claim 1 wherein one of said branch probes is positioned at a biological cell sample, and the other branch probe is positioned in the environs of the biological cell.

19. The apparatus of claim 1 wherein one of said branch probes is positioned at a first biological cell sample, and the other branch probe is positioned at a second biological cell that is interacting with the first biological cell.

20. The apparatus of claim 1 wherein one of said branch probes is positioned at a first biological cell sample, and the other branch probe is positioned at a second biological cell that is nonadjacent to the first biological cell.

21. The apparatus of claim 1 wherein said laser is operated to induce fluorescence light in the sample.

22. The apparatus of claim 1 wherein said apparatus is used in conjunction with an inductively-coupled plasma mass spectrometry (ICP-MS) system.

23. The apparatus of claim 1 wherein said apparatus is used in conjunction with a neutron capture therapy (NCT) system.

24. The apparatus of claim 1 wherein said apparatus is used in conjunction with an inductively-coupled plasma atomic emission spectrometry (ICP-AES) system.

25. The apparatus of claim 1 wherein said apparatus is used in conjunction with a laser microprobe mass analysis (LAMMA) system.

* * * * *